United States Patent [19]

Scheuermann et al.

[11] 4,139,532
[45] Feb. 13, 1979

[54] N-ACYLAMINONAPHTHALIMIDES

[75] Inventors: Horst Scheuermann; Albert Hettche, both of Ludwigshafen, Fed. Rep. of Germany

[73] Assignee: BASF Aktiengesellschaft, Ludwigshafen, Fed. Rep. of Germany

[21] Appl. No.: 686,368

[22] Filed: May 14, 1976

[51] Int. Cl.² .................. C07D 221/14; C09K 11/06; C07D 401/12; C07D 413/12
[52] U.S. Cl. ..................................... 546/99; 544/126; 544/237; 544/310; 544/316; 544/319; 544/333; 544/361; 8/1 D; 260/244.4; 546/9
[58] Field of Search .................. 260/281 N, 281 S

[56] References Cited

U.S. PATENT DOCUMENTS

| | | | |
|---|---|---|---|
| 3,625,947 | 12/1971 | Noguchi | 260/281 N |
| 3,697,525 | 10/1972 | Okada | 260/281 N |
| 3,798,224 | 3/1974 | Hotta | 260/281 N |
| 3,880,857 | 4/1975 | Schevermann | 260/281 N |
| 3,880,859 | 4/1975 | Schevermann et al. | 260/281 N |
| 3,941,791 | 3/1976 | Hill | 260/281 N |

FOREIGN PATENT DOCUMENTS 49-57049  6/1974  Japan ................. 260/281 N

OTHER PUBLICATIONS

Kasai et al., Chem. Abs. 72, 45001d (1970).

*Primary Examiner*—Mark L. Berch
*Attorney, Agent, or Firm*—Keil & Witherspoon

[57] ABSTRACT

Compounds of the formula:

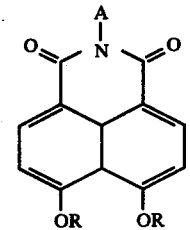

in which one R is identical with or different from the other R and each is alkyl, hydroxyalkyl, alkoxyalkyl, haloalkyl, cycloalkyl, aralkyl, aryl, N,N-dialkylaminoalkyl or quaternized N,N-dialkylaminoalkyl; A is

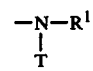

or

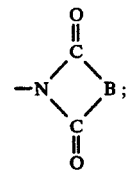

$R^1$ is hydrogen, substituted or unsubstituted alkyl, cycloalkyl, aralkyl, aryl or heteroaryl;

B is —CH=CH—, —CCl=CH—, —CCl=CCl—, —CH=CBr—, —CH₂—CH₂—, 1,2-phenylene, 1,8-naphthylene or 1,2-phenylene or 1,8-naphthylene bearing chloro, bromo, methoxy or ethoxy as a substituent; and T is acyl.

The compounds are eminently suitable as optical brighteners, particularly for polyesters and blends of polyester and cotton.

5 Claims, No Drawings

N-ACYLAMINONAPHTHALIMIDES

The invention relates to compounds of the formula (I):

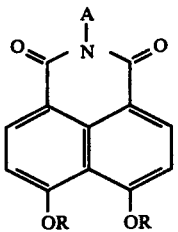

in which one R is identical with or different from the other R and each R is alkyl, hydroxylalkyl, alkoxyalkyl, haloalkyl, cycloalkyl, aralkyl, aryl, N,N-dialkylaminoalkyl or quaternized N,N-dialkylaminoalkyl; A is a radical of the formula

or

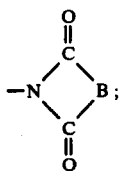

$R^1$ is hydrogen or substituted or unsubstituted alkyl, cycloalkyl, aralkyl, aryl or heteroaryl;

B is —CH=CH—, —CCl=CH—, —CCl=CCl—, —CH=CBr—, $CH_2$—$CH_2$— or 1,2-phenylene or 1,8-naphthylene either of which may bear chloro, bromo, methyl, ethyl, methoxy or ethoxy; and T is acyl.

Examples of radicals R are: alkyl or one to eight carbon atoms, hydroxyalkyl of two to six carbon atoms, alkoxyalkyl of a total of three to ten carbon atoms, chloroalkyl or bromoalkyl of two to six carbon atoms, cycloalkyl of five to seven carbon atoms, aralkyl of seven to ten carbon atoms, phenyl optionally bearing methyl, ethyl, methoxy, ethoxy, chloro or bromo as a substituent, N,N-dialkylaminoethyl or N,N-dialkylaminopropyl in each case of one to four carbon atoms in the alkyl and in either case the dialkylamino group may be formed by a saturated heterocyclic five-membered to seven membered ring and the said substituted amino groups may also be quaternized.

Specific examples of radicals R are:
$CH_3$, $C_2H_5$, $C_3H_7$, $C_4H_9$, $C_5H_{11}$, $C_6H_{13}$, $C_7H_{15}$, $C_8H_{17}$, $C_2H_4OH$, $C_3H_6OH$, $C_4H_8OH$, $C_5H_{10}OH$, $C_6H_{12}OH$, $C_2H_4OCH_3$, $C_2H_4OC_2H_5$, $C_2H_4OC_4H_9$, $C_3H_6OCH_3$, $C_3H_6OC_2H_5$, $C_3H_6OC_4H_9$, $C_4H_8OCH_3$, $C_4H_8OC_4H_9$, $C_6H_{12}OCH_3$, $C_6H_{12}OC_4H_9$, $C_2H_4Cl$, $C_3H_6Cl$, $C_2H_4Br$, $C_3H_6Br$, $C_4H_8Cl$, $C_6H_{12}Br$, $C_5H_9$, $C_6H_{11}$, $C_7H_{13}$, $CH_2$—$C_6H_5$, $C_2H_4C_6H_5$, $C_3H_6C_6H_5$, $C_4H_8C_6H_5$, $C_6H_4$—$CH_3$, $C_6H_4C_2H_5$, $C_6H_4$—$OCH_3$, $C_6H_4OC_2H_5$, $C_6H_4Cl$, $C_6H_4Br$, $C_2H_4N(CH_3)_2$, $C_2H_4N(C_2H_5)_2$, $C_2H_4N(C_3H_7)_2$, $C_2H_4N(C_4H_9)_2$, $C_3H_6N(CH_3)_2$, $C_3H_6N(C_2H_5)_2$, $C_3H_6N(C_4H_9)_2$,

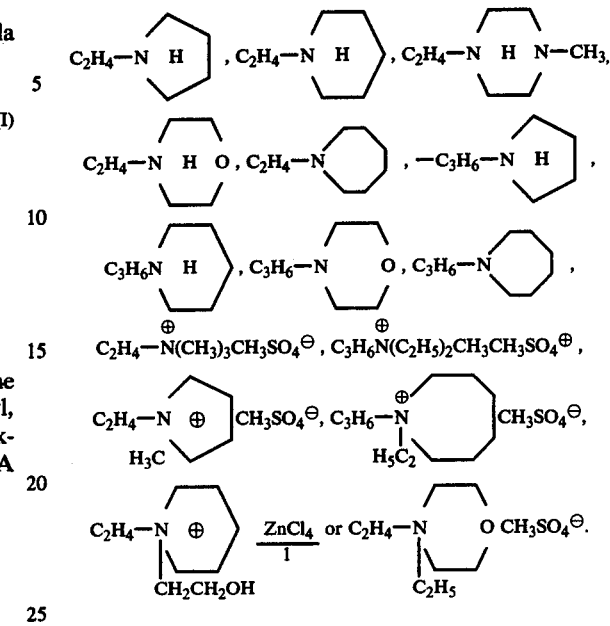

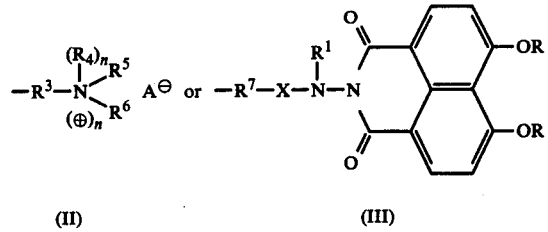

Acyl radicals T have the formula —X—$R^2$ in which X is a radical of the formula —CO— or —$SO_2$— and $R^2$ is hydrogen, unsubstituted or substituted alkyl, cycloalkyl, aralkyl, aryl, heteroalkyl, alkoxy, cycloalkoxy, aryloxy, alkylamino, arylamino or a radical of the formula (II) or (III):

$$-R^3-N\underset{(\oplus)_n}{\overset{(R_4)_n}{\underset{R^6}{\bigg|}}}R^5 \quad A^\ominus \quad \text{or} \quad -R^7-X-N-N$$

(II)   (III)

Examples of radicals $R^2$ are: alkyl of one to seventeen carbon atoms, chloroalkyl or bromoalkyl of one to eight carbon atoms, alkoxyalkyl of one to six carbon atoms in the alkoxy and one to eight carbon atoms in the alkyl, alkylaminoalkyl of one to six carbon atoms in the alkylamino and one to eight carbon atoms in the alkyl, dialkylaminoalkyl of two to ten carbon atoms in the dialkylamino and one to eight carbon atoms in the alkyl and the dialkylamino radical may be a saturated five-membered, six-membered or seven-membered ring, alkylmercaptoalkyl of one to six carbon atoms in the alkylmercapto radical and one to eight carbon atoms in the alkyl, phenyloxyalkyl or phenylthioalkyl of one to eight carbon atoms in the alkyl and the phenyl radical may bear $CH_3$, $CH_3O$, Cl or Br as a substituent, cycloalkyl of five to seven carbon atoms, aralkyl of seven to twelve carbon atoms, phenyl optionally bearing methyl, ethyl, methoxy, ethoxy, chloro, bromo or hydroxysulfonyl as a substituent, pyridyl, pyrimidinyl, furyl, pyrrolyl, thienyl, alkoxy of one to eight carbon atoms, cycloalkoxy of five to seven carbon atoms, phenoxy optionally bearing $CH_3$, $C_2H_5$, $OCH_3$, $OC_2H_5$, chloro or bromo as a substituent, $(C_2H_4O)_nB$ where n is 1, 2 or 3 and B is alkyl of one to four carbon atoms, alkylamino or dialkylamino of one to eight carbon atoms in the alkyl radicals, phenylamino or naphthylamino optionally bearing chloro, bromo, methyl or ethyl as a substituent in either case, or a radical of the formula (II).

Examples of radicals $R^3$ are alkylene groups of one to eight carbon atoms; specific examples are $CH_3$, $C_2H_4$, $C_3H_6$, $C_5H_{10}$, $C_6H_{12}$, $C_8H_{16}$, $CH_2CH-CH_3$ or

Suitable examples of $R^5$ and $R^6$ are hydrogen, alkyl of one to eight carbon atoms, hydroxyalkyl of two or three carbon atoms, cyclohexyl, phenylethyl and, together with the nitrogen, a saturated or unsaturated five-membered to seven-membered heteroalkyl ring and the unsaturated heterocycles may be cationic.

Specific examples of unsaturated heterocycles are:

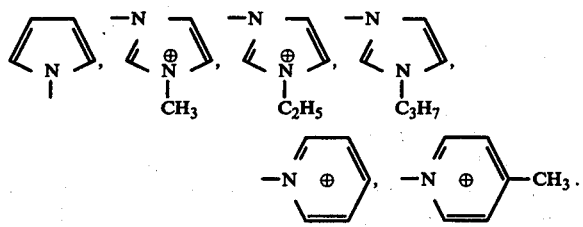

Examples of further radicals $R^5$ and $R^6$ in addition to those already specified are:

$CH_3$, $C_2H_5$, $C_3H_7$, $C_4H_9$, $C_5H_{11}$, $C_6H_{13}$, $C_7H_{15}$, $C_8H_{17}$,

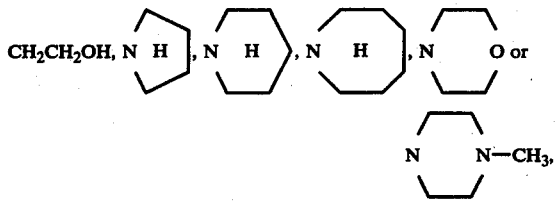

and $R^5$ and $R^6$ may be identical or different.

Particular examples of $R^4$ are: hydrogen, methyl, ethyl, butyl, β-hydroxyethyl, β-hydroxypropyl or benzyl.

n is zero or 1 and the anion $A^{(-)}$ when n is 1 may be a cationic heterocyclic radical or a simple or complex inorganic or organic anion such as $Cl^{(-)}$, $Br^{(-)}$, $I^{(-)}$, $SO_4^{(-)(-)}$, $CH_3SO_4^{(-)}$, $C_2H_5SO_4^{(-)}$, $C_6H_5SO_3^{(-)}$, $CH_3C_6H_4SO_3^{(-)}$, $SCN^{(-)}$, $CH_3COO^{(-)}$, $HCOO^{(-)}$, $CO_3^{(-)(-)}$ or $ZnCl_4^{(-)(-)}$.

Examples of radicals $R^7$ are:

$-CH_2-$, $C_2H_4-$, $C_3H_6-$, $-C_4H_8-$, $-C_6H_{12}-$,

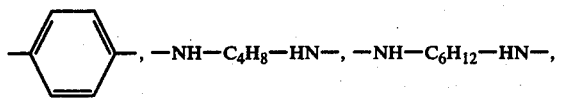, $-NH-C_4H_8-HN-$, $-NH-C_6H_{12}-HN-$, $-NHC_8H_{16}HN-$,

-continued

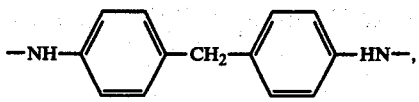

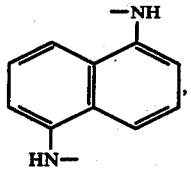

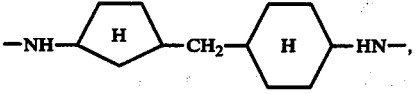

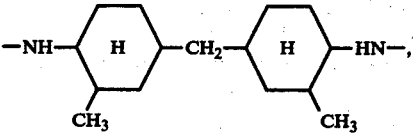

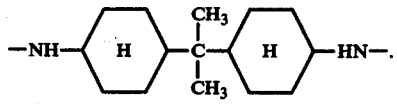

Specific examples of $R^2$ are:
hydrogen, $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$, $C_{11}H_{23}$, $C_{12}H_{25}$, $C_{13}H_{27}$, $C_{14}H_{29}$, $C_{15}H_{31}$, $C_{16}H_{33}$, $C_{17}H_{35}$, $(CH_2)_7-CH=CH-CH-C_8H_{17}$, $CH_2Cl$, $CH_2Br$, $C_2H_4Cl$, $C_2H_4Br$, $C_3H_6Cl$, $C_4H_8Cl$, $C_5H_{10}Cl$, $C_6H_{12}Cl$, $C_5H_{10}Br$, $C_6H_{12}Br$, $C_8H_{16}Cl$, $CH_2O-CH_3$, $CH_2-OC_2H_5$, $CH_2-O-C_4H_9$, $CH_2-O-C_6H_{13}$, $C_2H_4OCH_3$, $C_3H_6-OC_2H_5$, $C_4H_8OC_4H_9$, $C_6H_{12}OCH_3$, $C_7H_{14}OC_2H_5$, $CH_2-NHCH_3$, $CH_2-NH-C_2H_5$, $CH_2-NH-C_4H_9$, $CH_2-NH-C_6H_{13}$, $C_2H_4-NH-C_4H_9$, $C_4H_8NHC_6H_{13}$, $C_6H_{12}-NH-C_2H_5$, $CH_2-N(CH_3)_2$, $CH_2-N(C_2H_5)_2$, $CH_2-N(C_4H_9)_2$, $CH_2-NCH_3C_2H_5$, $CH_2-NCH_3C_2H_5$, $CH_2-NCH_3C_6H_{13}$, $C_2H_4-N(CH_3)_2$, $C_4H_8-N(C_2H_5)_2$, $C_6H_{12}NCH_3C_2H_5$,

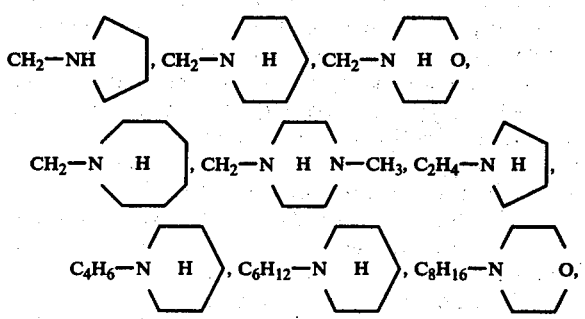

$CH_2-S-CH_3$, $CH_2-S-C_4H_9$, $CH_2-S-C_2H_5$, $C_4H_8-S-CH_3$, $C_6H_{12}-S-C_2H_5$, $CH_2-O-C_6H_5$, $CH_2-O-C_6H_4CH_3$, $CH_2-O-C_6H_4Cl$, $CH_2-OC_6H_4OCH_3$, $C_2H_4OC_6H_5$, $C_4H_8-O-C_6H_4CH_3$, $C_3H_6-S-C_6H_5$, $C_2H_4SC_6H_4CH_3$, $CH_2-S-C_6H_3Cl_2$, $CH_2-S-C_6H_4Br$, $OCH_3$, $OC_2H_5$, $OC_3H_7$, $OC_4H_9$, $OC_5H_{11}$, $OC_6H_{13}$, $OC_8H_{17}$, $OC_2H_4OCH_3$, $OC_2H_4OC_2H_5$, $OC_2H_4OC_2H_5$, $OC_2H_4OC_4H_9$, $O(C_2H_4O)_2CH_3$, $O(C_2H_4O)_2-C_2H_5$, $O(C_2H_4O)_2C_4H_9$, $O(C_2H_4O)_3-CH_3$, $NHCH_3$, $NHC_2H_5$, $NHC_4H_9$, $NHC_5H_{11}$, $NHC_6H_{13}$, $NHC_7H_{15}$, $NHC_8H_{17}$, $N(CH_3)_2$, $N(C_2H_5)_2$, $N(C_4H_9)_2$.

In addition to hydrogen, $R^1$ may denote the same radicals as for R and the protons of hydroxyl groups may if desired be replaced by acyl radicals T. $R^1$ and T together with the nitrogen may form a radical:

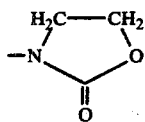

Examples of other radicals $R^1$ are:

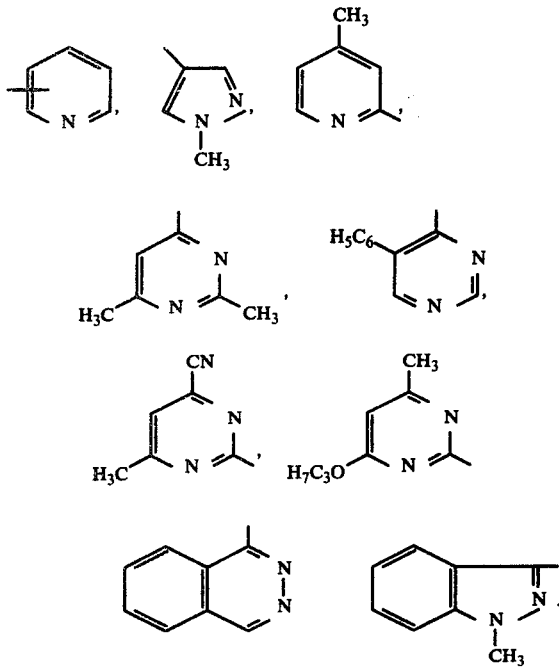

Terms such as propyl and butyl in the context of the present invention also include the isomeric groups isopropyl, isobutyl and tertiary-butyl.

Particular industrial importance attaches to compounds in which X is a radical of the formula —CO; $R^2$ is alkyl of three to seventeen carbon atoms, chloroalkyl or bromoalkyl of one to six carbon atoms, alkoxyalkyl of one to four carbon atoms in the alkoxy and one to five carbon atoms in the alkyl, alkylaminoalkyl of one to four carbon atoms in the alkylamino and one to four carbon atoms in the alkyl, dialkylaminoalkyl of one to eight carbon atoms in the dialkylamino and one to four carbon atoms in the alkyl and the dialkylamino radical may be a saturated five-membered, six-membered or seven-membered ring, cycloalkyl of five to seven carbon atoms, aralkyl of seven to ten carbon atoms, phenyl which may bear methyl, ethyl, methoxy, ethoxy, chloro, bromo or hydroxysulfonyl as a substituent, alkoxy of one to six carbon atoms, cyclohexyloxy, phenoxy, toluyloxy, alkylamino of one to eight carbon atoms, a radical of the formula (II); $R^1$ is hydrogen, alkyl of one to four carbon atoms, $C_2H_4OH$, $C_3H_6OH$ or

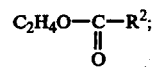

and

R is alkyl of one to four carbon atoms or alkoxyalkyl of a total of from three to six carbon atoms.

Particularly preferred compounds have the formula (Ia):

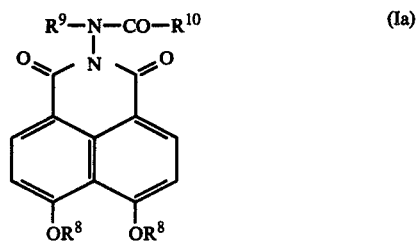

in which
$R^8$ is alkyl of one to four carbon atoms;
$R^9$ is alkyl of one to eight carbon atoms; and
$R^{10}$ is alkyl of one to fifteen carbon atoms, chloroalkyl or bromoalkyl of one to four carbon atoms, dialkylaminoalkyl with one to four carbon atoms in the alkyl in each case, or pyrrolidinoalkyl, piperidinoalkyl, morpholinoalkyl, piperazinoalkyl, N-methylpiperazinoalkyl, imidazoliumalkyl, pyridiniumalkyl or picoliniumalkyl of one to four carbon atoms in the alkyl.

The new compounds of the formula (I) are colorless to pale yellow and are suitable as optical brighteners for fibers and thermoplastic materials, e.g. of polyamide, cellulose ester, or acrylonitrile polymers and particularly polyesters, cotton and mixtures of polyester and cotton. The treated materials exhibit an intense greenish blue to bluish violet fluorescence in daylight or under ultraviolet radiation. For the application of the new compounds to the said materials, the thermosol process (for polyesters), the padding process (for cotton) and the exhaustion method (for polyamide and cellulose esters) are particularly suitable.

The following reactions may for example be carried out for the production of the new compounds:

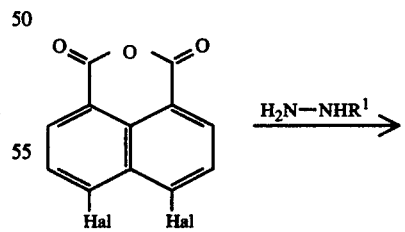

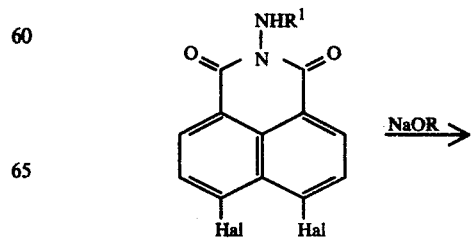

-continued

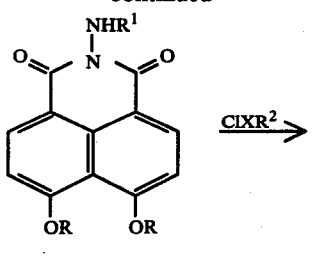

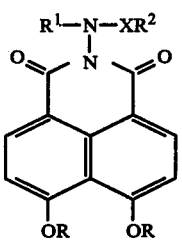

Hal is chloro or bromo.

Compounds having external amino groups or ammonium groups are obtained for example as follows:

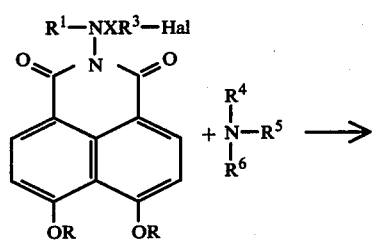

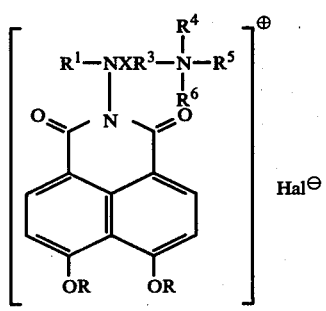

R to $R^6$ and X have the meanings given above.

The reactions are known in principle and proceed analogously under comparable conditions. Details will be found in the Examples in which parts and percentages are by weight unless otherwise stated.

EXAMPLE 1

43 parts of N-methylamino-4,5-dimethoxynaphthalimide and 22 parts of potassium carbonate are suspended in 300 parts of N-methylpyrrolidone. 50 parts of palmityl chloride is dripped in at from 40° to 50° C. while stirring and stirring is continued for another hour. After the whole has cooled it is stirred into 1000 parts of ice and water and suction filtered. The product is recrystallized from alcohol. 70 parts of a compound is obtained which has the following structure:

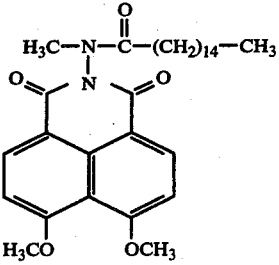

It has a melting poind of from 175° to 177° C.

N-methylamino-4,5-dimethoxynaphthalimide necessary for the production of this acyl compound is prepared as follows: 125 parts of N-methylamino-4,5-dichloronaphthalimide, 1300 parts of methanol and 60 parts of tetraglycol dimethyl ether are placed in a vessel. 360 parts of sodium methylate solution (30%) is allowed to drip in at refluxing temperature in three hours. The whole is stirred for another five hours at 65° C. After the whole has cooled the product is suction filtered, washed with 2000 parts of water and dried. 95 parts of N-methylamino-4,5-dimethoxynaphthalimide is obtained which melts at from 252° to 255° C.

N-methylamino-4,5-dichloronaphthalimide is obtained in the following way: 400 parts of 4,5-dichloronaphthalic anhydride is suspended in 1500 parts of glacial acetic acid. The whole is heated to 90° to 100° C. and 84 parts of N-methylhydrazine is dripped in. Stirring is carried on for seven hours at the said temperature. After cooling the whole is stirred into 7000 parts of water and the product is suction filtered and dried.

390 parts of N-methylamino-4,5-dichloronaphthalimide is obtained; it has a melting point of 246° to 248° C.

EXAMPLE 2

43 parts of N-methylamino-4,5-dimethoxynaphthalimide and 22 parts of potassium carbonate are suspended in 300 parts of N-methylpyrrolidone. 30 parts of lauryl chloride is dripped in at 40° to 50° C. The whole is stirred for one hour at the said temperature, allowed to cool and poured into 1000 parts of ice and water, and the product is suction filtered and recrystallized from alcohol. 60 parts of the following compound is obtained:

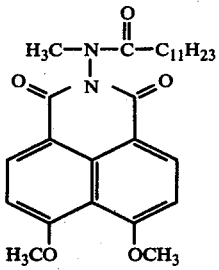

It has a melting point of 173° to 175° C.

EXAMPLE 3

21.5 parts of N-methylamino-4,5-dimethoxynaphthalimide and 17 parts of potassium carbonate are suspended in 150 parts of N-methylpyrrolidone. 20.3 parts of 2-ethylhexanoyl chloride is dripped in at 50° C. The whole is stirred for another hour, cooled, stirred into 500 parts of ice and water, suction filtered and recrystallized from alcohol. 23 parts of the following compound is obtained:

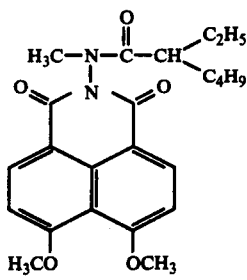

It has a melting point of 185° to 186° C.

EXAMPLE 4

A compound of the following structure is obtained analogously to Example 3 with propionyl chloride:

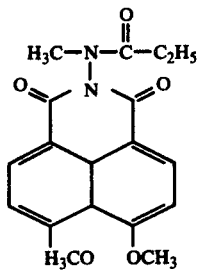

It has a melting point of 260° to 263° C.

EXAMPLE 5

A compound of the following structure is obtained analogously to Example 3 with cinnamyl chloride:

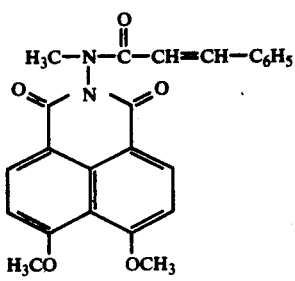

It has a melting point of 223° to 225° C.

EXAMPLE 6

32 parts of N-methylamino-4,5-dimethoxynaphthalimide, 200 parts of acetic anhydride and 3 parts of concentrated sulfuric acid are stirred for thirty minutes at 70° to 80° C. and then for ninety minutes at 100° to 110° C. After cooling the product is suction filtered and recrystallized from N-methylpyrrolidone. 25 parts of the following compound is obtained:

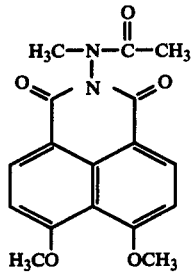

It has a melting point of 347° to 350° C.

EXAMPLE 7

57 parts of N-methylamino-4,5-dimethoxynaphthalimide, 700 parts of N-methylpyrrolidone and 24 parts of pyridine are placed in a vessel. 44 parts of $\beta$-chloropropionyl chloride is dripped in at ambient temperature. The whole is stirred for another two hours, stirred into 3000 parts of ice-water and suction filtered.

68 parts of a compound of the following structure is obtained:

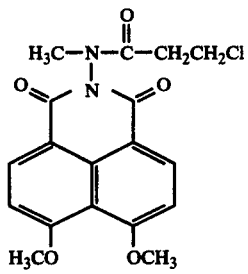

It has a melting point of 233° to 236° C. after it has been recrystallized from ethyl glycol.

EXAMPLE 8

21.5 parts of N-methylamino-4,5-dimethoxynaphthalimide, 150 parts of N-methylpyrrolidone and 17 parts of potassium carbonate are placed in a vessel. 17 parts of 4-chlorobutyryl chloride is dripped in at 50° C. while stirring. Stirring is continued for another ninety minutes. After the whole has been cooled it is stirred into 500 parts of ice and water. The solid product is suction filtered and recrystallized from toluene.

20 parts of the following compound is obtained:

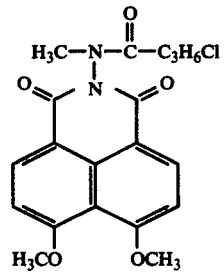

It has a melting point of 200° to 202° C.

EXAMPLE 9

14.3 parts of N-methylamino-4,5-dimethoxynaphthalimide and 4 parts of pyridine are suspended in 150 parts of N-methylpyrrolidone. 30 parts of stearyl chloride is dripped in at ambient temperature, the whole is stirred for four hours at 40° C. and then cooled, stirred into 500 parts of ice-water and suction filtered.

After recrystallization from alcohol 22 parts of the following compound is obtained:

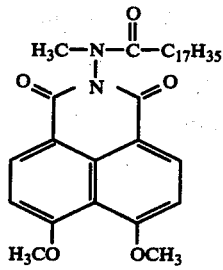

The melting point is 158° to 160° C.

EXAMPLE 10

31.6 parts of N-(hydroxyethylamino)-4,5-dimethoxynaphthalimide and 17.4 parts of pyridine are suspended in 200 parts of N-methylpyrrolidone. 37.8 parts of lauryl chloride is dripped in and the whole is stirred for another hour at ambient temperature. It is then worked up by stirring into ice, suction filtered and recrystallization from alcohol.

60 parts of the following compound is obtained:

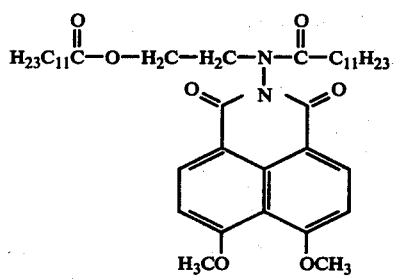

It has a melting point of 63° to 70° C.

N-(hydroxyethylamino)-4,5-dimethoxynaphthalimide is obtained as follows: 110 parts of N-(hydroxyethylamino)-4,5-dichloronaphthalimide, 1200 parts of methanol and 50 parts of tetraethylene glycol dimethyl ether are placed in a vessel. 250 parts of sodium methylate solution (30%) is dripped in at 65° C. and the whole is stirred for a total of eight hours at this temperature. After cooling the product is suction filtered, washed with 800 parts of water and dried. 92 parts of N-(hydroxyethylamino)-4,5-dimethoxynaphthalimide is obtained having a melting point of 227° to 228° C.

N-(hydroxyethylamino)-4,5-dichloronaphthalimide is obtained from 4,5-dichlorophthalic anhydride and hydroxyethylhydrazine in glacial acetic acid. It has a melting point of 236° to 238° C.

EXAMPLE 11

26 parts of N-(hydroxyethylamino)-4,5-dimethoxynaphthalimide and 14.2 parts of pyridine are introduced into 165 parts of N-methylpyrrolidone. 31.2 parts of palmityl chloride is dripped in at 20° C. and the whole is stirred for one hour at ambient temperature and for another three hours at 50° C. It is then allowed to cool, stirred into ice and a pale yellow compound of the following structure is obtained:

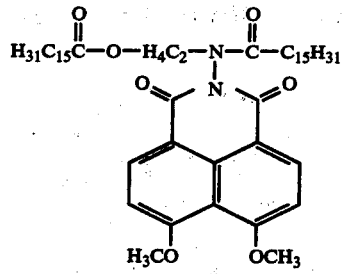

It exhibits an intense bluish violet fluorescence in alcoholic solution in daylight. It has a melting point of 60° to 70° C.

EXAMPLE 12

14.3 parts of N-methylamino-4,5-dimethoxynaphthalimide is suspended in 150 parts of N-methylpyrrolidone. 10 parts of b-butylchlorocarbonic ester is dripped in at 50° C. and the whole is stirred for another three hours at this temperature, then allowed to cool, and stirred into ice-water, and the precipitate is suction filtered and recrystallized from alcohol. 15 parts of a compound of the following structure is obtained:

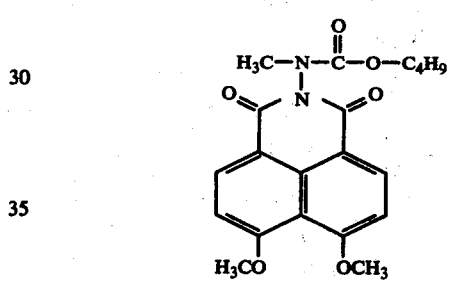

It has a melting point of 160° to 165° C.

EXAMPLE 13

14.3 parts of N-methylamino-4,5-dimethoxynaphthalimide, 4 parts of pyridine and 150 parts of N-methylpyrrolidone are placed in a vessel. 42 parts of oleyl chloride is dripped in. The whole is stirred for another four hours at 40° C. It is then precipitated on ice, suction filtered and recrystallized from alcohol. 21 parts of the following compound is obtained:

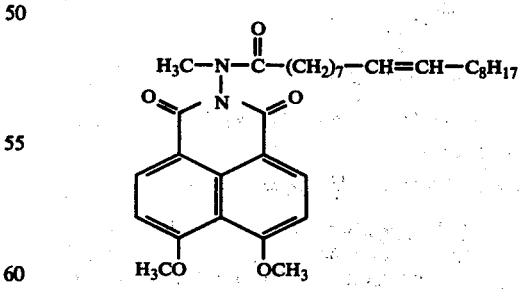

It has a melting poind of 145° to 148° C.

EXAMPLE 14

A mixture of 18.8 parts of N-(N'-methyl-N'-β-chloropropionylamino)-4,5-dimethoxynaphthalimide, 170 parts of methanol and 20 parts of 40% aqueous dimethylamine solution is stirred for five hours at 65° C. The whole is allowed to cool. The precipitated solid is suction filtered. 16 parts of a compound of the following structure is obtained:

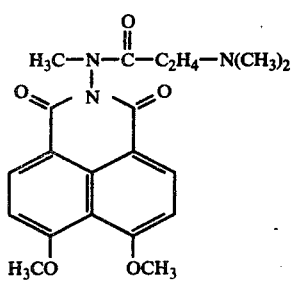

It has a melting point of 268° to 270° C.

EXAMPLE 15

18 parts of N-methylamino-4,5-dimethoxynaphthalimide is introduced into 200 parts of N-methylpyrrolidone. 14 parts of n-propylchlorocarbonic ester is dripped in at ambient temperature in two hours. The whole is stirred for another two hours. After having been cooled it is stirred into ice-water and the precipitate is suction filtered and recrystallized from methanol. 19 parts of the following compound is obtained:

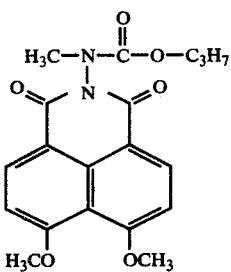

It has a melting point of 173° to 175° C.

EXAMPLE 16

A mixture of 18.8 parts of N-(N'-methyl-N'-β-chloropropionylamino)-4,5-dimethoxynaphthalimide, 170 parts of methanol, 10 parts of water and 20 parts of morpholine is stirred for seven hours at 65° C. and allowed to cool, and the precipitate is suction filtered and 17 parts of the following compound is obtained:

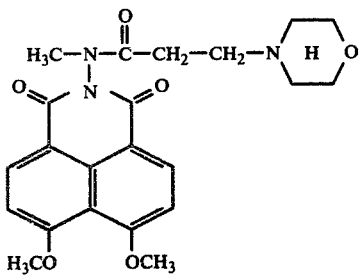

It has a melting point of 240° to 245° C.

EXAMPLES 17 AND 18

In the manner described in Example 16 the following two products can be obtained with piperidine or hexamethylenimine:

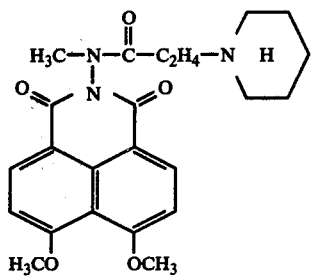

melting point 177° to 178° C.

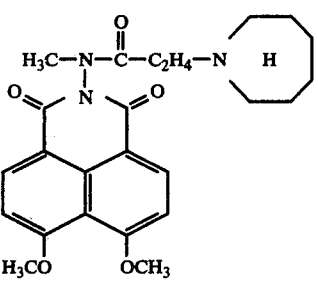

melting point 255° to 260° C.

EXAMPLE 19

63.2 parts of N-(hydroxyethylamino)-4,5-dimethoxynaphthalimide and 34.7 parts of pyridine are introduced into 700 parts of N-methylpyrrolidone. 88 parts of β-chloropropionyl chloride is dripped in in one hour at ambient temperature. The whole is then stirred at 40° to 50° C. for another 190 minutes. After having been cooled the whole is stirred into ice-water and the precipitate is suction filtered and dried. 80 parts of the following compound is obtained (melting point 135° to 138° C.):

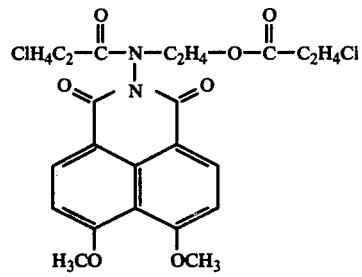

EXAMPLE 20

The following compound (melting point 203° to 207° C.) is obtained with acetyl chloride by the method of Example 19:

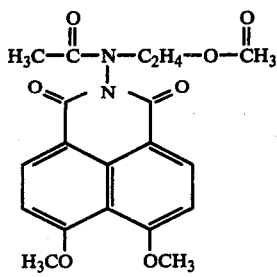

EXAMPLE 21

The following compound (melting point 112° to 113° C.) is obtained with 2-ethylhexanoyl chloride by the method of Example 19:

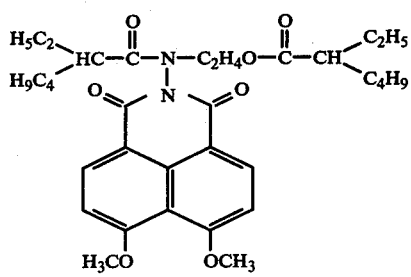

EXAMPLE 22

The following compound (melting point 178° to 180° C.) is obtained with propionyl chloride by the method of Example 19:

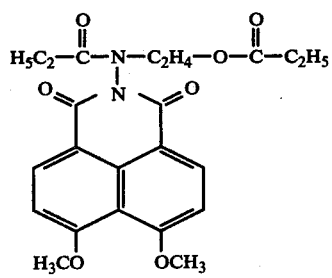

EXAMPLE 25

A mixture of 9 parts of N-(N'-methyl-N'-β-chloropropionylamino)-4,5-dimethoxynaphthalimide, 100 parts of methanol and 40 parts of an aqueous 30% trimethylamine solution is stirred for ten hours at refluxing temperature. The following compound is obtained in a quantitative yield:

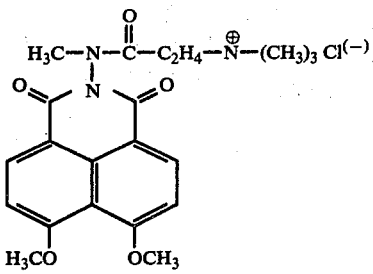

It dissolves completely in water and exhibits intense blue fluorescence in daylight or under an ultraviolet lamp.

EXAMPLE 24

19.5 parts of N-(N'-methyl-N'-β-morpholinopropionylamino)-4,5-dimethoxynaphthalimide is dissolved in 150 parts of toluene. 8 parts of dimethyl sulfate is allowed to drip in at 80° C., the whole is stirred at this temperature for another three hours and allowed to cool and the precipitate deposited is suction filtered. 18 parts of the following compound is obtained:

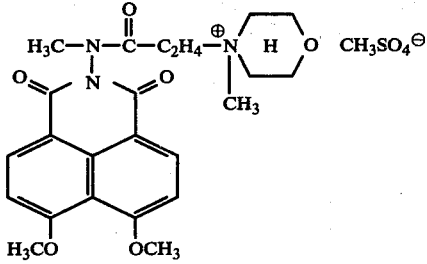

It dissolves completely in water and exhibits intense blue fluorescence in daylight or under an ultraviolet lamp.

EXAMPLE 25

19.5 parts of N-(N'-methyl-N'-β-piperidinopropionylamino)-5,4-dimethoxynaphthalimide is dissolved in 150 parts of toluene. 10 parts of diethyl sulfate is allowed to drip in at 80° C., the whole is stirred for another four hours at this temperature, allowed to cool and the deposited precipitate is suction filtered. 17 parts of the following compound is obtained:

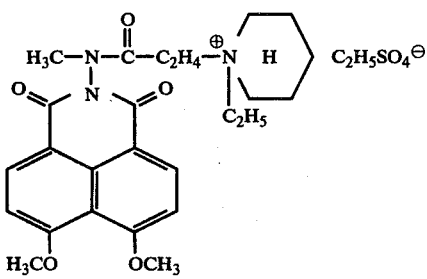

It has good solubility in water and gives intense blue fluorescence in daylight or under ultraviolet radiation.

EXAMPLE 26

18 parts of N-(N'-methyl-N'-α-dimethylaminoacetylamino)-4,5-dimethoxynaphthalimide is dissolved in 150 parts of toluene. 9 parts of dimethyl sulfate is dripped in at 80° C. The whole is stirred at this temperature for another two hours. It is then allowed to cool, the deposited precipitate is suction filtered and 20 parts of the following compound is obtained:

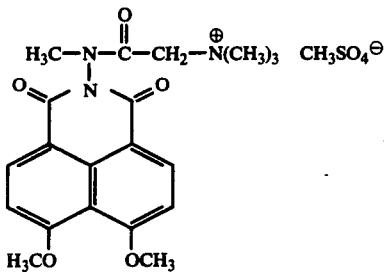

It has good solubility in water and gives intense blue fluorescence in daylight or under ultraviolet radiation.

EXAMPLE 27

15 parts of N-methylamino-4,5-dichloronaphthalimide, 100 parts of butanol, 10 parts of methanol and 6 parts of tetraglycol dimethyl ether are placed in a vessel. 40 parts of a solution of sodium methylate (30%) is allowed to drip in in two hours at 70° C. The whole is stirred for another five hours at 70° C. After cooling it is suction filtered, washed with water, dried and suspended in 100 parts of N-methylpyrrolidone together with 8 parts of pyridine. 16 parts of 2-ethylhexanoyl is dripped in at ambient temperature and stirred at 40° C. for another three hours. After the whole has cooled it is stirred into ice-water and suction filtered. 18 parts of a mixture of the following three compounds in which R is $CH_3$ and/or $C_4H_9$ is obtained:

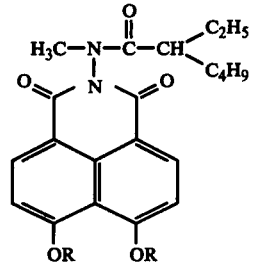

When the compounds are dissolved in alcohol the solution exhibits intense bluish violet fluorescence in daylight or under an ultraviolet lamp.

The compounds characterised by an indication of their substituents in the following Table are also obtained analogously to the said methods:

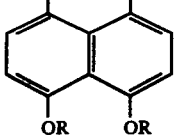

| Bsp. | R | $R^1$ | $R^2$ | X |
|---|---|---|---|---|
| 28 | $CH_3$ | $CH_3$ | 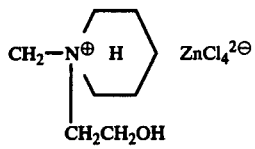 | —CO— |
| 29 | $CH_3$ | $CH_3$ | $CH_2N(C_2H_5)_2$ | —CO— |
| 30 | $CH_3$ | $CH_3$ | $CH_2-\overset{\oplus}{N}(C_2H_5)_2CH_3$ $CH_3SO_4^\ominus$ | —CO— |
| 31 | $CH_3$ | $C_6H_4Cl$ | $C_7H_{15}$ | —CO— |
| 32 | $C_2H_5$ | 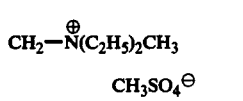 | $OC_4H_9$ | —CO— |
| 33 | $C_2H_5$ | 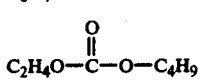 | $OC_3H_7$ | —CO— |
| 34 | $C_2H_5$ | 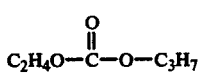 | 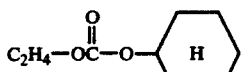 | —CO— |
| 35 | $CH_3$ | 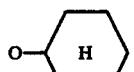 | 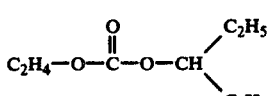 | —CO— |
| 36 | $CH_3$ | $CH_3$ | $NHC_4H_9$ | —CO— |

-continued

| | | | | |
|---|---|---|---|---|
| 37 | CH₃ | CH₃ | NHC₆H₅ | —CO— |
| 38 | CH₃ | C₂H₄—O—C(=O)—NH—C₄H₉ | NH—C₄H₉ | —CO— |
| 39 | CH₃ | C₂H₄—O—C(=O)—NH—C₆H₅ | NH—C₆H₅ | —CO— |
| 40 | CH₃ | CH₃ | C₃H₇ | —CO— |
| 41 | CH₃ | CH₃ | C₄H₉ | —CO— |
| 42 | CH₃ | C₂H₅ | C₅H₁₁ | —CO— |
| 43 | CH₃ | C₂H₅ | C₆H₁₃ | —CO— |
| 44 | CH₃ | C₃H₇ | C₈H₁₇ | —CO— |
| 45 | CH₃ | C₃H₇ | C₉H₁₉ | —CO— |
| 46 | CH₃ | C₄H₉ | C₁₁H₂₃ | —CO— |
| 47 | CH₃ | CH₃ | C₁₂H₂₅ | —CO— |
| 48 | CH₃ | C₄H₉ | C₁₃H₂₇ | —CO— |
| 49 | CH₃ | C₄H₉ | C₁₄H₂₉ | —CO— |
| 50 | CH₃ | C₄H₉ | C₁₆H₃₃ | —CO— |
| 51 | CH₃ | C₅H₁₁ | CH₂Br | —CO— |
| 52 | CH₃ | C₅H₁₁ | C₂H₄Br | —CO— |
| 53 | CH₃ | C₅H₁₁ | C₄H₈Cl | —CO— |
| 54 | CH₃ | C₃H₇ | C₅H₁₀Cl | —CO— |
| 55 | CH₃ | C₆H₁₃ | C₆H₁₂Cl | —CO— |
| 56 | CH₃ | C₅H₉ | C₅H₁₀Br | —CO— |
| 57 | CH₃ | C₂H₅ | C₈H₁₆Cl | —CO— |
| 58 | CH₃ | C₂H₅ | CH₂OCH₃ | —CO— |
| 59 | CH₃ | C₈H₁₇ | CH₂—O—C₂H₅ | —CO— |
| 60 | CH₃ | C₁₂H₂₅ | C₂H₄OCH₃ | —CO— |
| 61 | CH₃ | C₂H₅ | C₃H₆OC₂H₅ | —CO— |
| 62 | CH₃ | CH₃ | C₆H₁₂OCH₃ | —CO— |
| 63 | CH₃ | C₂H₅ | C₄H₉OCH₃ | —CO— |
| 64 | CH₃ | CH₃ | C₅H₁₀OCH₃ | —CO— |
| 65 | CH₃ | C₂H₅ | CH₂—NH—CH₃ | —CO— |
| 66 | CH₃ | CH₃ | CH₂NHC₅H₁₁ | —CO— |
| 67 | CH₃ | C₂H₅ | C₂H₄NHC₄H₉ | —CO— |
| 68 | C₂H₅ | CH₃ | C₄H₈NHC₆H₁₃ | —CO— |
| 69 | C₃H₇ | C₂H₅ | CH₂N(CH₃)₂ | —CO— |
| 70 | C₄H₉ | C₂H₅ | CH₂N(C₂H₅)₂ | —CO— |
| 71 | CH₃ | CH₃ | CH₂N(C₄H₉)₂ | —CO— |
| 72 | CH₃ | CH₃ | CH₂NCH₃C₂H₅ | —CO— |
| 73 | C₆H₁₃ | CH₃ | C₂H₄N(C₂H₅)₂ | —CO— |
| 74 | CH₃ | C₄H₉ | C₄H₈N(C₃H₇)₂ | —CO— |
| 75 | CH₃ | C₄H₉ | 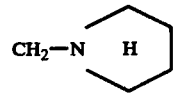 CH₂—N (piperidinyl) | —CO— |
| 76 | C₂H₅ | CH₃ | CH₂—N (morpholinyl, H O) | —CO— |

-continued

| | | | | |
|---|---|---|---|---|
| 77 | C₃H₇ | CH₃ | CH₂—N⟨piperidine⟩H | —CO— |
| 78 | C₂H₅ | CH₃ | CH₂—N⟨piperazine⟩H N—CH₃ | —CO— |
| 79 | C₂H₅ | C₄H₉ | C₂H₄—N⟨piperidine⟩H | —CO— |
| 80 | CH₃ | CH₃ | C₄H₆—N⟨piperidine⟩H | —CO— |
| 81 | CH₃ | CH₃ | C₆H₁₂—N⟨morpholine⟩H O | —CO— |
| 82 | C₂H₅ | CH₃ | C₈H₁₆—N⟨morpholine⟩H O | —CO— |
| 83 | C₂H₅ | C₆H₁₃ | CH₂—SCH₃ | —CO— |
| 84 | CH₃ | C₈H₁₇ | —CH₂—S—C₄H₉ | —CO— |
| 85 | CH₃ | C₂H₄OCH₃ | C₂H₄SC₂H₅ | —CO— |
| 86 | CH₃ | C₃H₆OCH₃ | C₄H₈—S—CH₃ | —CO— |
| 87 | CH₃ | C₃H₆OC₄H₉ | C₆H₁₂SC₂H₅ | —CO— |
| 88 | CH₃ | C₆H₁₂OCH₃ | CH₂—OC₆H₅ | —CO— |
| 89 | C₂H₅ | CH₂—C₆H₅ | CH₂—OC₆H₄Cl | —CO— |
| 90 | C₂H₅ | C₂H₄—C₆H₅ | C₂H₄OC₆H₅ | —CO— |
| 91 | CH₃ | C₃H₆C₆H₅ | C₃H₆SC₆H₅ | —CO— |
| 92 | C₂H₅ | C₆H₄CH₃ | C₂H₄SC₆H₄CH₃ | —CO— |
| 93 | CH₃ | C₆H₅ | CH₂—S—C₆H₄Cl | —CO— |
| 94 | CH₃ | C₆H₄OCH₃ | CH₂SC₆H₃Cl₂ | —CO— |
| 95 | CH₃ | C₆H₄Br | OCH₃ | —CO— |
| 96 | C₂H₅ | C₆H₄Br | OC₃H₇ | —CO— |
| 97 | C₂H₅ | C₂H₄N(CH₃)₂ | CH₂—N(CH₃)₂ | —CO— |
| 98 | C₃H₇ | C₂H₄N(C₂H₅) | C₂H₄—N(C₂H₅)₂ | —CO— |
| 99 | C₂H₅ | C₂H₄—N⟨piperidine⟩H | CH₂—N⟨piperidine⟩H | —CO— |
| 100 | C₂H₅ | C₂H₄—N⟨morpholine⟩H O | CH₂—N⟨morpholine⟩H O | —CO— |
| 101 | C₂H₅ | C₂H₄—N⟨piperidine⟩H | C₃H₆—N⟨piperidine⟩H | —CO— |

-continued

| # | | | | |
|---|---|---|---|---|
| 102 | CH₃ | C₂H₄—N(piperazine H)N—CH₃ | C₆H₁₂—N(piperazine H)N—CH₃ | —CO— |
| 103 | C₂H₄OCH₃ | CH₃ | OC₄H₉ | —CO— |
| 104 | C₂H₄OC₂H₅ | C₂H₅ | OC₅H₁₁ | —CO— |
| 105 | C₃H₆OC₂H₅ | C₂H₅ | OC₆H₁₃ | —CO— |
| 106 | C₆H₁₂OCH₃ | CH₃ | OC₂H₄OCH₃ | —CO— |
| 107 | C₂H₄Cl | H | OC₂H₄OC₄H₉ | —CO— |
| 108 | CH₃ | H | O(C₂H₄O)₃—CH₃ | —CO— |
| 109 | C₂H₅ | H | NHCH₃ | —CO— |
| 110 | C₂H₅ | H | NHC₂H₅ | —CO— |
| 111 | C₃H₇ | H | NHC₄H₉ | —CO— |
| 112 | C₄H₉ | H | NHC₅H₁₁ | —CO— |
| 113 | C₄H₉ | H | NHC₆H₁₃ | —CO— |
| 114 | C₄H₉ | CH₃ | NHC₈H₁₇ | —CO— |
| 115 | C₂H₅ | CH₃ | N(CH₃)₂ | —CO— |
| 116 | C₃H₇ | CH₃ | N(C₄H₉)₂ | —CO— |
| 117 | C₂H₅ | C₄H₉ | CH₂—N⁺(CH₃)₂ Cl⁻ | —CO— |
| 118 | C₃H₇ | C₄H₉ | CH₂—N⁺(pyrrolidine)CH₃ CH₃SO₄⁻ | —CO— |
| 119 | C₄H₉ | C₂H₅ | C₂H₄—N⁺(piperidine)CH₃ CH₃SO₄⁻ | —CO— |
| 120 | C₂H₅ | C₂H₅ | CH₂N⁺(C₂H₅)₂CH₃ CH₃SO₄⁻ | —CO— |
| 121 | C₂H₅ | C₄H₉ | CH₂—N⁺(C₄H₉)₂CH₃ H₃CSO₄⁻ | —CO— |
| 122 | CH₃ | C₂H₅ | C₄H₉—N⁺(CH₃)₃ Cl | —CO— |
| 123 | CH₃ | C₂H₅ | C₈H₁₆N⁺(CH₃)₃ CH₃SO₄⁻ | —CO— |
| 124 | CH₃ | C₂H₅ | C₆H₁₂N⁺(imidazolium)CH₃ Cl⁻ | —CO— |
| 125 | CH₃ | C₂H₅ | CH₂—N(imidazolium)C₂H₅ Cl⁻ | —CO— |
| 126 | CH₃ | C₂H₅ | CH₂—N⁺(pyridinium) Cl⁻ | —CO— |
| 127 | C₄H₉ | CH₃ | CH₂—N(imidazolium)CH₂C₆H₅ Cl⁻ | —CO— |
| 128 | C₂H₅ | CH₃ | CH₂—N(2-methylimidazolium)CH₃ Cl⁻ | —CO— |

-continued

| # | R1 | R2 | R3 | X |
|---|---|---|---|---|
| 129 | $C_2H_5$ | $CH_3$ | $C_2H_4-N{=}{\bigoplus}$ pyrazolium with $C_3H_7$, $Br^{\ominus}$ | $-CO-$ |
| 130 | $CH_3$ | $C_8H_{17}$ | N-methylpyrrolidinium $CH_3SO_4^{\ominus}$ | $-CO-$ |
| 131 | $CH_3$ | $C_7H_{15}$ | $CH_2-\overset{\oplus}{N}(CH_3)_3$ | $-CO-$ |
| 132 | $CH_3$ | 6-methylpyridin-2-yl | $C_2H_5$ | $-CO-$ |
| 133 | $CH_3$ | 1-methyl-4-pyrazolyl | $CH_3$ | $-CO-$ |
| 134 | $CH_3$ | 6-methylpyridin-3-yl | $C_5H_{11}$ | $-CO-$ |
| 135 | $C_2H_5$ | 2-cyano-pyrimidinyl vinyl | $CH_3$ | $-CO-$ |
| 136 | $C_4H_9$ | 1H-indazol-3-yl | $C_5H_{11}$ | $-CO-$ |
| 137 | $C_4H_9$ | dimethylpyrimidinyl vinyl | $C_{15}H_{31}$ | $-CO-$ |
| 138 | $CH_3$ | 6-methylpyridin-2-yl | $C_{11}H_{23}$ | $-CO-$ |
| 139 | $CH_3$ | 6-methylpyridin-3-yl (N-CH3) | $C_7H_{15}$ | $-CO-$ |
| 140 | $C_4H_9$ | $C_2H_6O\overset{O}{\overset{\|}{C}}-CH_3$ | $CH_3$ | $-CO-$ |
| 141 | $C_3H_7$ | $C_3H_7O\overset{O}{\overset{\|}{C}}-C_2H_5$ | $C_2H_5$ | $-CO-$ |
| 142 | $C_4H_9$ | $C_2H_6O\overset{O}{\overset{\|}{C}}-C_{11}H_{23}$ | $C_{11}H_{23}$ | $-CO-$ |
| 143 | $C_3H_7$ | $C_6H_{12}O\overset{O}{\overset{\|}{C}}-C_7H_{15}$ | $C_7H_{15}$ | $-CO-$ |
| 144 | $C_2H_5$ | $C_4H_8O\overset{O}{\overset{\|}{C}}-C_5H_{11}$ | $C_5H_{11}$ | $-CO-$ |
| 145 | $C_2H_5$ | $C_8H_{16}O\overset{O}{\overset{\|}{C}}-C_2H_5$ | $C_2H_5$ | $-CO-$ |
| 146 | $C_4H_9$ | $C_2H_6OC_{17}H_{35}$ | $C_{17}H_{35}$ | $-CO-$ |
| 147 | $CH_3; C_2H_5$ | $CH_3$ | $CH_3$ | $-CO-$ |
| 148 | $CH_3; C_4H_9$ | $CH_3$ | $C_2H_5$ | $-CO-$ |
| 149 | $CH_3; C_2H_5$ | $CH_3$ | $C_7H_{15}$ | $-CO-$ |
| 150 | $CH_3; C_3H_7$ | H | $C_7H_{15}$ | $-CO-$ |
| 151 | $CH_3; C_2H_5$ | H | $C_{11}H_{23}$ | $-CO-$ |
| 152 | $CH_3; C_4H_9$ | H | $C_{15}H_{31}$ | $-CO-$ |
| 153 | $C_2H_5; C_4H_9$ | H | $C_3H_7Cl$ | $-CO-$ |
| 154 | $C_2H_5; C_4H_9$ | H | $CH_2Cl$ | $-CO-$ |
| 155 | $C_2H_5; C_4H_9$ | $C_2H_5$ | $CH_2-N(CH_3)_2$ | $-CO-$ |

-continued

| # | | | | |
|---|---|---|---|---|
| 156 | C₂H₅;CH₃ | C₃H₇ | CH₂—N(C₂H₅)₂ | —CO— |
| 157 | CH₃; C₄H₉ | C₄H₉ | C₂H₄N(CH₃)₂ | —CO— |
| 158 | CH₃; C₂H₅ | C₆H₁₃ | C₃H₆N(C₄H₉)₂ | —CO— |
| 159 | CH₃; C₃H₇ | C₈H₁₇ | C₆H₁₂N(CH₃)₂ | —CO— |
| 160 | CH₃; C₂H₅ | C₅H₁₁ | CH₂Br | —CO— |
| 161 | CH₃; C₂H₅ | C₂H₄OCH₃ | C₇H₁₅ | —CO— |
| 162 | CH₃; C₂H₅ | C₃H₆OC₂H₅ | C₇H₁₅ | —CO— |
| 163 | CH₃; C₂H₅ | C₆H₁₂OCH₃ | CH₃ | —CO— |
| 164 | CH₃ | C₆H₅ | C₂H₅ | —CO— |
| 165 | CH₃ | C₆H₅ | C₃H₇ | —CO— |
| 166 | CH₃ | C₆H₅ | C₇H₁₅ | —CO— |
| 167 | CH₃ | C₆H₅ | C₁₁H₂₃ | —CO— |
| 168 | CH₃ | C₆H₅ | C₁₅H₃₁ | —CO— |
| 169 | CH₃ | C₆H₄CH₃ | C₁₇H₃₅ | —CO— |
| 170 | CH₃ | C₆H₄CH₃ | CH₂Cl | —CO— |
| 171 | CH₃ | CH₃ | CH₂—N(CH₃)₂ | —CO— |
| 172 | CH₃ | C₆H₅ | | —CO— |
| 173 | CH₃ | C₆H₄Cl | CH₂—N⟨piperidine⟩H | |

| 174 | CH₃ | CH₃ | CH₃ | —SO₂— |
| 175 | CH₃ | CH₃ | C₆H₅ | —SO₂— |
| 176 | CH₃ | C₂H₅ | C₆H₄CH₃ | —SO₂— |
| 177 | CH₃ | C₄H₉ | C₆H₄—CH₃ | —SO₂— |
| 178 | CH₃ | C₄H₉ | CH₃ | —SO₂— |
| 179 | CH₃ | C₆H₅ | C₆H₅ | —SO₂— |
| 180 | CH₃ | C₆H₄CH₃ | C₆H₄CH₃ | —SO₂— |
| 181 | CH₃ | C₆H₅ | C₆H₄CH₃ | —SO₂— |
| 182 | CH₃ | C₆H₄Cl | CH₃ | —SO₂— |
| 183 | CH₃ | C₆H₄Cl | C₆H₅ | —SO₂— |
| 184 | CH₃ | CH₃ | C₆H₅SO₃H | —CO— |
| 185 | CH₃ | C₄H₉ | C₆H₅SO₃H | —CO— |
| 186 | CH₃ | C₂H₅ | (pyrimidine ring) | —CO— |

| 187 | CH₃ | C₂H₅ | (furan ring) | —CO— |

| 188 | CH₃ | CH₃ | (pyrrole NH ring) | —CO— |

| 189 | CH₃ | CH₃ | (thiophene ring) | —CO— |

| 190 | CH₃ | CH₃ | (pyridine ring) | —CO— |

| 191 | CH₃ | C₂H₄—O—CO—C₂H₄—N⁺⟨piperidine⟩H / CH₃ · CH₃SO₄⁻ | C₂H₄—N⁺⟨piperidine⟩H / CH₃ · CH₃SO₄⁻ | —CO— |

| 192 | CH₃ | C₂H₄—O—CO—C₂H₄—N⁺(CH₃)₃ · CH₃SO₄⁻ | C₂H₄N(CH₃)₃CH₃SO₄⁻ | —CO— |

| 193 | CH₃ | C₂H₄—O—CO—C₂H₄—N⁺(C₂H₅)₂ / CH₃ · CH₃SO₄⁻ | C₂H₄—N⁺(C₂H₅)₂ / CH₃ · CH₃SO₄⁻ | —CO— |

| 194 | CH₃ | C₂H₄—O—CO—C₂H₄—N⁺⟨morpholine⟩ / CH₃ | C₂H₄—N⁺⟨morpholine⟩ / CH₃ · CH₃SO₄⁻ | —CO— |

-continued

| | | | | |
|---|---|---|---|---|
| 195 | CH₃ | C₂H₄—O—C(=O)—C₂H₄—N(azepane)H | C₂H₄—N(azepane)H | —CO— |
| 196 | CH₃ | C₂H₄O—C(=O)—C₂H₄N(C₄H₉)₂ | C₂H₄—N(C₄H₉)₂ | —CO— |
| 197 | CH₃ | C₂H₄O—C(=O)—C₂H₄N(C₆H₁₃)₂ | C₂H₄N(C₆H₁₃)₂ | —CO— |
| 198 | CH₃ | C₂H₄OH | C₂H₄N(CH₃)₂ | —CO— |
| 199 | CH₃ | CH₃ | CH₂N(CH₃)₂ | —CO— |
| 200 | CH₃ | C₂H₄OH | C₂H₄N(morpholine)H,O | —CO— |
| 201 | CH₃ | C₂H₄OH | C₂H₄—N(C₄H₉)₂ | —CO— |
| 202 | CH₃ | C₂H₄OH | C₃H₆—N(C₆H₁₃)₂ | —CO— |
| 203 | CH₃ | C₂H₄OH | C₂H₄—N⁺(C₂H₅)(CH₃) CH₃SO₄⁻ | —CO— |
| 204 | CH₃ | C₂H₄OH | C₂H₄—N⁺(CH₃)₃ CH₃SO₄⁻ | —CO— |
| 205 | CH₃ | C₆H₅ | C₂H₄—N(CH₃)₂ | —CO— |
| 206 | CH₃ | C₆H₄CH₃ | CH₂—N(C₂H₅)₂ | —CO— |
| 207 | CH₃ | C₆H₄Cl | C₂H₄N⁺(CH₃)₃ CH₃SO₄⁻ | —CO— |
| 208 | CH₃ | C₆H₅ | C₂H₄N⁺(C₂H₅)₂(CH₃) CH₃SO₄⁻ | —CO— |
| 209 | CH₃ | C₆H₄CH₃ | C₄H₈—N=C(CH₃)—N⁺(CH₃)— (imidazolinium) Cl⁻ | —CO— |
| 210 | CH₃ | C₆H₄CH₃ | C₂H₄N⁺(pyridinium) Br⁻ | —CO— |
| 211 | CH₃ | C₆H₄CH₃ | CH₂—N⁺(pyridinium) Br⁻ | —CO— |
| 212 | CH₃ | C₆H₁₁ | C₂H₄—N(C₂H₅)₂ | —CO— |
| 213 | CH₃ | C₆H₁₁ | C₂H₄N(C₄H₉)₂ | —CO— |
| 214 | CH₃ | C₈H₁₇ | C₂H₄N⁺(CH₃)₃ CH₃SO₄⁻ | —CO— |
| 215 | CH₃ | C₃H₆OH | CH₃ | —CO— |
| 216 | CH₃ | C₄H₇OH | C₇H₁₅ | —CO— |
| 217 | CH₃ | C₆H₁₂OH | C₂H₄N(CH₃)₂ | —CO— |
| 218 | CH₃ | C₂H₄Br | C₂H₄Cl | —CO— |
| 219 | CH₃ | C₂H₄Br | CH₂Cl | —CO— |
| 220 | C₂H₄Cl | CH₃ | CH₃ | —CO— |

-continued

| | | | | |
|---|---|---|---|---|
| 221 | $C_3H_6Br$ | $CH_3$ | $C_7H_{15}$ | —CO— |
| 222 | $C_2H_4N(CH_3)_2$ | $CH_3$ | $C_2H_5$ | —CO— |
| 223 | $C_2H_4N(C_2H_5)_2$ | $CH_3$ | $C_3H_7$ | —CO— |
| 224 | $C_2H_4N\begin{pmatrix}\\H\\\end{pmatrix}O$ | $CH_3$ | $C_2H_5$ | —CO— |
| 225 | $C_2H_4-\overset{\oplus}{N}\begin{pmatrix}\\H\\CH_3\end{pmatrix}$ $CH_3SO_4^{\ominus}$ | $CH_3$ | $CH_3$ | —CO— |
| 226 | $C_3H_6-\overset{\oplus}{N}\begin{pmatrix}\\H\\CH_3\end{pmatrix}$ $CH_3SO_4^{\ominus}$ | $CH_3$ | $C_2H_5$ | —CO— |
| 227 | $C_2H_4N(C_4H_9)_2$ | $CH_3$ | $C_3H_7$ | —CO— |
| 228 | $C_3H_6-\overset{\oplus}{N}\begin{pmatrix}\\H\\CH_3\end{pmatrix}$ | $CH_3$ | $C_4H_9$ | —CO— |
| 229 | $C_2H_4C_6H_5$ | $C_3H_7$ | $C_2H_5$ | —CO— |

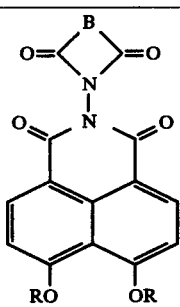

| Bsp. | R | B |
|---|---|---|
| 230 | $CH_3$ | —$CH_2$=$CH_2$— |
| 231 | $CH_3$ | —CH=CH— |
| 232 | $CH_3$ | —CCl=CH— |
| 233 | $CH_3$ | —CCl=CCl— |
| 234 | $CH_3$ | naphthalene-$OCH_3$ |
| 235 | $C_2H_5$ | naphthalene-$OC_2H_5$ |

| | | | |
|---|---|---|---|
| 236 | CH₃ | | (naphthalene with two CH₃ and two Cl substituents) |
| 237 | CH₃ | | (naphthalene with two CH₃ and two OCH₃ substituents, H₃CO, OCH₃) |
| 238 | C₂H₅ | | (dimethylbenzene) |
| 239 | C₄H₉ | | (dimethyl-chlorobenzene, Cl) |
| 240 | CH₃ | | (dimethyl-methoxybenzene, OCH₃) |

(structure: RO–naphthalimide–N(R¹)–N–C(O)–R⁷–C(O)–N–N(R¹)–naphthalimide–OR, with OR groups)

| Bsp. | R | R¹ | R⁷ |
|---|---|---|---|
| 241 | CH₃ | CH₃ | —CH₂— |
| 242 | CH₃ | CH₃ | —C₂H₄— |
| 243 | CH₃ | CH₃ | —C₃H₆— |
| 244 | CH₃ | CH₃ | —C₄H₈— |
| 245 | CH₃ | CH₃ | —C₆H₁₂— |
| 246 | CH₃ | CH₃ | (para-phenylene) |
| 247 | CH₃ | CH₃ | —NH—C₄H₈HN— |
| 248 | CH₃ | CH₃ | NH—C₆H₁₂HN— |
| 249 | CH₃ | C₂H₅ | NH—C₈H₁₆—HN— |
| 250 | CH₃ | C₂H₅ | (methyl-phenylene with —NH and —HN— substituents) |

-continued

| | | | |
|---|---|---|---|
| 251 | CH₃ | C₄H₉ | NH—⟨⟩—CH₂—⟨⟩—HN— |
| 252 | CH₃ | C₄H₉ | —NH / naphthalene / HN— |
| 253 | CH₃ | C₂H₅ | NH—⟨H⟩—CH₂—⟨H⟩—HN— |
| 254 | CH₃ | CH₃ | NH—⟨H⟩—CH₂—⟨H⟩—HN, with CH₃ substituents |
| 255 | CH₃ | CH₃ | NH—⟨H⟩—C(CH₃)₂—⟨H⟩—HN— |

In the Table: Bsp. = Example.

Fluorescence properties of solutions in ultraviolet radiation and daylight:

The compounds 28 to 30, 65 to 82, 117 to 131, 155 to 159, 172, 173, 191 to 214 and 222 to 228 dissolve in 2% acetic acid. The solutions have a blue fluorescence.

The compounds 31 to 64, 95 to 96, 140 to 154, 160 to 171, 215, 216, 218 to 221 and 229 dissolve in alcohol. They have a bluish violet fluorescence.

The compounds 83 to 94 and 103 to 116 dissolve in alcohol and have a blue fluorescence.

The compounds 97 to 102 dissolve in 2% acetic acid and have a greenish blue fluorescence.

The compounds 132 to 139, 174 to 183 and 230 to 255 are siluble in dimethylformamide and have a blue fluorescence.

The compounds 184 to 190 dissolve in dimethylformamide and have a greenish blue fluorescence.

EXAMPLE 256

6 parts of N-isopropylamino-4,5-dimethoxynaphthalimide and 5 parts of potassium carbonate are introduced into 30 parts of N-methylpyrrolidone. 3 parts of acetyl chloride is dripped in at 40–50° C., and stirring is continued for another two hours. Precipitation is effected by means of water and then the whole is suction filtered. There is obtained 6 parts of the compound

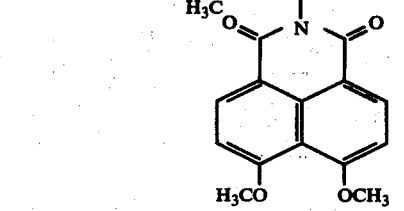

which, after recrystallization from dimethylformamide, has a melting point of 269°–270° C.

N-isopropylamino-4,5-dimethoxynaphthalimide is obtained by reaction of N-isopropylamino-4,5-dichloronaphthalimide with sodium methylate in methanol. Melting point: 238° C.

N-isopropylamino-4,5-dichloronaphthalimide can be prepared by reaction of 4,5-dichloronaphthalic anhydride with isopropylhydrazine in glacial acetic acid. Melting point: 180°–182° C.

EXAMPLE 257

The procedure of Example 256 is followed except that propionyl chloride is used instead of acetyl chloride. There is obtained the following compound:

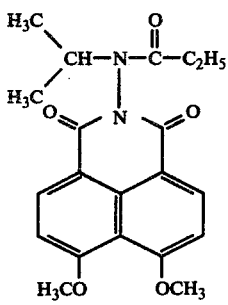

After recrystallization from isopropanol its melting point is 123°–126° C.

EXAMPLE 258

6.5 parts of N-isobutylamino-4,5-dimethoxynaphthalimide and 5 parts of potassium carbonate are introduced into 30 parts of N-methylpyrrolidone. 3 parts of acetyl chloride are dripped in at 40°–50° C., and stirring is continued for two hours. Precipitation is effected with water and then suction filtration is carried out. There is obtained 6 parts of the following compound:

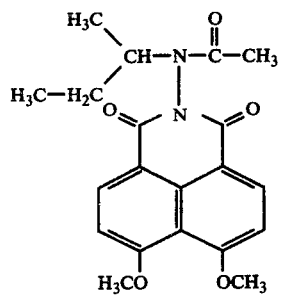

After recrystallization from methyl glycol it has a melting point of 259°–260° C. N-isobutylamino-4,5-dimethoxynaphthalimide is obtained by reaction of N-isobutylamino-4,5-dichloronaphthalimide with sodium methylate in methanol. Melting point: 212°–214° C.

N-isobutylamino-4,5-dichloronaphthalimide can be prepared by reaction of 4,5-dichloronaphthalic anhydride with isobutylbutylhydrazine in glacial acetic acid. Melting point: 163°–167° C.

When proceeding analogously to the methods indicated, the compounds given in the table are obtained:

| Ex. | R | $R^1$ | $R^2$ | Flourescence in alcohol |
|---|---|---|---|---|
| 259 | $CH_3$ | $-CH(CH_3)CH_3$ | H | bluish violet |
| 260 | $CH_3$ | $-CH(CH_3)CH_2-CH_3$ | H | " |
| 261 | $C_2H_5$ | $-CH(CH_3)CH_3$ | H | " |
| 262 | $C_4H_9$ | $-CH(CH_3)CH_3$ | H | " |
| 263 | $C_2H_4OCH_3$ | $-CH(CH_3)CH_3$ | H | " |
| 264 | $C_2H_5$ | $-CH(CH_3)CH_3$ | $CH_3$ | " |
| 265 | $C_4H_9$ | $-CH(CH_3)CH_3$ | $CH_3$ | " |
| 266 | $C_2H_4OCH_3$ | $-CH(CH_3)CH_3$ | $CH_3$ | " |
| 267 | $CH_3$ | $-CH(CH_3)C_2H_5$ | $C_2H_5$ | " |
| 268 | $C_2H_5$ | $-CH(CH_3)C_2H_5$ | H | " |
| 269 | $C_4H_9$ | $-CH(CH_3)C_2H_5$ | H | " |
| 270 | $C_2H_4OCH_3$ | $-CH(CH_3)C_2H_5$ | H | " |
| 271 | $C_2H_5$ | $-CH(CH_3)C_2H_5$ | $CH_3$ | " |
| 272 | $C_4H_9$ | $-CH(CH_3)C_2H_5$ | $CH_3$ | " |
| 273 | $C_2H_4OCH_3$ | $-CH(CH_3)C_2H_5$ | $CH_3$ | " |
| 274 | $C_2H_5$ | $-CH(CH_3)C_2H_5$ | $C_2H_5$ | " |
| 275 | $C_4H_9$ | $-CH(CH_3)C_2H_5$ | $C_2H_5$ | " |
| 276 | $C_2H_4OCH_3$ | $-CH(CH_3)C_2H_5$ | $C_2H_5$ | " |
| 277 | $CH_3$ | $-CH(CH_3)C_2H_5$ | $C_3H_7$ | " |
| 278 | $CH_3$ | $-CH(CH_3)CH_3$ | $C_3H_7$ | " |
| 279 | $CH_3$ | $-CH(CH_3)CH_3$ | $C_4H_9$ | " |
| 280 | $CH_3$ | $-CH(CH_3)C_2H_5$ | $C_7H_{15}$ | " |
| 281 | $CH_3$ | $-CH(CH_3)C_3H_7$ | H | " |

-continued

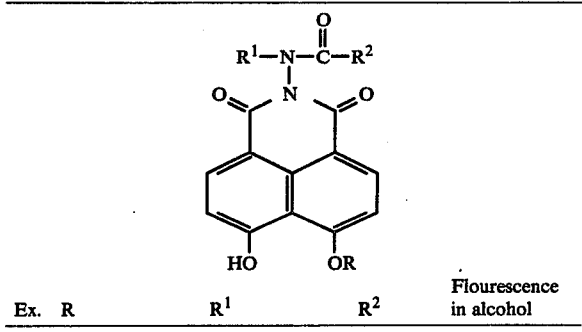

| Ex. | R | R¹ | R² | Flourescence in alcohol |
|---|---|---|---|---|
| 282 | C₂H₅ | -CH(CH₃)(C₃H₇) | H | " |
| 283 | C₂H₄OC₂H₅ | -CH(CH₃)(C₃H₇) | H | " |
| 284 | CH₃ | -CH(CH₃)(C₃H₇) | CH₃ | " |
| 285 | CH₃ | -CH(CH₃)(C₃H₇) | C₂H₅ | " |
| 286 | CH₃ | -CH(CH₃)(C₃H₇) | C₃H₇ | " |
| 287 | CH₃ | -CH(CH₃)(C₃H₇) | C₇H₁₅ | " |
| 288 | CH₃ | -CH(CH₃)-CH(CH₃)(CH₃) | H | " |
| 289 | CH₃ | -CH(CH₃)-CH(CH₃)(CH₃) with extra CH₃ | " | |
| 290 | CH₃ | -CH(C₂H₅)(C₂H₅) | H | " |
| 291 | CH₃ | -CH(C₂H₅)(C₂H₅) | CH₃ | " |
| 292 | CH₃ | -CH₂-C(CH₃)(CH₃)(CH₃) | H | " |
| 293 | CH₃ | -CH₂-C(CH₃)(CH₃)(CH₃) | CH₃ | " |
| 294 | CH₃ | cyclopentyl | H | " |
| 295 | CH₃ | cyclopentyl | CH₃ | " |
| 296 | CH₃ | cyclohexyl | H | " |
| 297 | CH₃ | cyclohexyl | CH₃ | " |
| 298 | CH₃ | cyclohexyl | C₂H₅ | " |

-continued

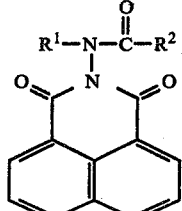

| Ex. | R | R¹ | R² | Flourescence in alcohol |
|---|---|---|---|---|
| 299 | CH₃ | 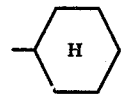 | C₂H₅ | " |

We claim:

1. A compound of the formula:

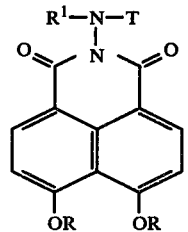

in which one R is identical with or different from the other R and each is alkyl of one to six carbon atoms or alkoxyalkyl of one to four carbon atoms in the alkoxy and two to six carbon atoms in the alkyl; R¹ is branched alkyl of three to six carbon atoms; and T is alkanoyl of one to six carbon atoms.

2. A compound as claimed in claim 1 of the formula

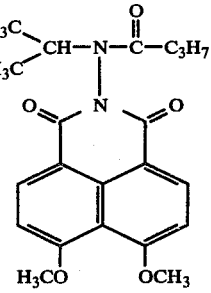

3. A compound as claimed in claim 1 of the formula

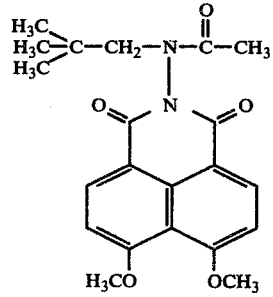

4. A compound as claimed in claim 1 in which R is methyl or ethyl; and
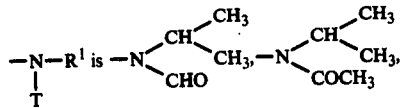
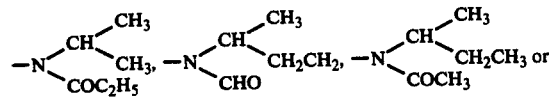
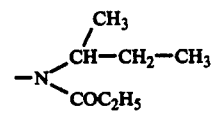
5. A compound as claimed in claim 1 in which R is alkyl of one to four carbon atoms.
* * * * *